US008975242B2

(12) United States Patent
Fawzi et al.

(10) Patent No.: US 8,975,242 B2
(45) Date of Patent: *Mar. 10, 2015

(54) TIGECYCLINE COMPOSITIONS AND METHODS OF PREPARATION

(75) Inventors: Mahdi B. Fawzi, Morristown, NJ (US); Tianmin Zhu, Monroe, NY (US); Syed M. Shah, East Hanover, NJ (US)

(73) Assignee: Wyeth LLC, New York, NY (US)

( * ) Notice: Subject to any disclaimer, the term of this patent is extended or adjusted under 35 U.S.C. 154(b) by 956 days.

This patent is subject to a terminal disclaimer.

(21) Appl. No.: 13/011,164

(22) Filed: Jan. 21, 2011

(65) Prior Publication Data

US 2011/0118216 A1 May 19, 2011

Related U.S. Application Data

(63) Continuation of application No. 11/374,330, filed on Mar. 13, 2006, now Pat. No. 7,879,828.

(60) Provisional application No. 60/661,030, filed on Mar. 14, 2005.

(51) Int. Cl.
| | | |
|---|---|---|
| *A01N 37/18* | (2006.01) | |
| *A01N 43/42* | (2006.01) | |
| *A61K 31/65* | (2006.01) | |
| *A61K 31/44* | (2006.01) | |
| *A61K 9/08* | (2006.01) | |
| *A61K 9/00* | (2006.01) | |
| *A61K 9/19* | (2006.01) | |
| *A61K 47/26* | (2006.01) | |

(52) U.S. Cl.
CPC ............... *A61K 9/08* (2013.01); *A61K 9/0019* (2013.01); *A61K 9/19* (2013.01); *A61K 31/65* (2013.01); *A61K 47/26* (2013.01)
USPC .............................. 514/154; 514/53; 514/291

(58) Field of Classification Search
USPC ............................................ 514/53, 154, 291
See application file for complete search history.

(56) References Cited

U.S. PATENT DOCUMENTS

| | | | |
|---|---|---|---|
| 3,026,248 | A | 3/1962 | Noseworthy et al. |
| 3,106,512 | A | 10/1963 | Hill et al. |
| 3,145,228 | A | 8/1964 | Schach von Wittenau et al. |
| 3,219,529 | A | 11/1965 | Nash et al. |
| 4,038,315 | A | 7/1977 | Tobkes |
| 5,122,519 | A | 6/1992 | Ritter |
| 5,494,903 | A | 2/1996 | Hlavka et al. |
| 5,538,954 | A | 7/1996 | Koch et al. |
| 5,908,838 | A | 6/1999 | Gans |
| 7,879,828 | B2 | 2/2011 | Fawzi et al. |
| 2003/0171340 | A1 | 9/2003 | Isbister |
| 2005/0020610 | A1 | 1/2005 | Zhang et al. |
| 2005/0148553 | A1 | 7/2005 | Testa et al. |
| 2006/0094668 | A1 | 5/2006 | Raible et al. |

FOREIGN PATENT DOCUMENTS

| | | |
|---|---|---|
| CL | 2257-04 | 7/2005 |
| CN | 1390550 A | 1/2003 |
| EP | 1 645 277 A1 | 4/2006 |
| GB | 901107 | 7/1962 |
| GB | 2 414 668 A | 12/2005 |
| WO | 01/19362 A2 | 3/2001 |
| WO | WO 02/12170 A1 | 2/2002 |
| WO | WO 02/055731 A2 | 7/2002 |
| WO | WO 02/096354 A2 | 12/2002 |
| WO | WO 03/005971 A2 | 1/2003 |
| WO | WO 03/066064 A2 | 8/2003 |
| WO | WO 2004/038000 A2 | 5/2004 |
| WO | WO 2004/078111 A2 | 9/2004 |
| WO | 2005/004874 A1 | 1/2005 |
| WO | 2006/099258 A1 | 9/2006 |
| WO | WO 2006/130431 A1 | 12/2006 |

OTHER PUBLICATIONS

Babinchak, T. et al. "The efficacy and safety of tigecycline for the treatment of complicated intra-abdominal infections: analysis of pooled clinical trial data" *Clin. Infect. Dis.* 41(Suppl 5):S354-S367 (Sep. 1, 2005).

Baird-Bellaire, S.J. et al. "Pharmacokinetics (PK) of tigecycline (TGC) in patients with hepatic impairment" *Basic & Clinical Pharm. Toxicol.* 97(Suppl. 1):86, Abstr. 318 (2005).

Beidenbach et. al. "In vitro antimicrobial activity of GAR-936 tested against antibiotic-resistant gram-positive blood stream infection isolates and strains producing extended-spectrum beta-lactamases" *Diagn. Microbiol. Infect. Dis.* 40(4):173-177 (Aug. 2001).

Betriu, C. et. al. "In Vitro Activities of Tigecycline against Erythromycin-Resistant *Streptococcus pyogenes* and *Streptococcus agalactiae*: Mechanisms of Macrolide and Tetracycline Resistance" *Antimicrobial Agents & Chemotherapy* 48:323-325 (2004).

Boucher, H.W. et al. "In vitro activity of GAR-936 against gram-positive bacteria" 39th ICAAC Abstracts, American Society for Microbiology, Sep. 26-29, 1999, San Francisco, CA; Abstr. 406, p. 300 (1999).

Boucher, H.W. et al. "In Vitro Activities of the Glycylcycline GAR-936 against Gram-Positive Bacteria" *Antimicrobial Agents & Chemotherapy* 44:2225-2229 (2000).

Bradford, P.A. "Tigecycline: A First in Class Glycylcycline" *Clinical Microbiology Newsletter* 26:163-168 (2004).

Bryant, S.G. et al. "Increased frequency of doxycycline side effects" *Pharmacotherapy* 7(4):125-129 (1987).

Caswell, A.H. et al. "Selectivity of cation chelation to tetracyclines: evidence for special conformation of calcium chelate" *Biochem. Biophys. Res. Commun.* 43(3):625-630 (May 7, 1971).

(Continued)

*Primary Examiner* — Yong Chong
(74) *Attorney, Agent, or Firm* — A. David Joran

(57) ABSTRACT

The present invention relates to novel tigecycline compositions with improved stability in both solid and solution states and processes for making these compositions. These compositions comprise tigecycline, a suitable carbohydrate, and an acid or buffer.

9 Claims, No Drawings

(56) References Cited

OTHER PUBLICATIONS

Chin, T-F. et al. "Drug diffusion and bioavailability: tetracycline metallic chelation" Am. J. Hosp. Pharm. 32(6):625-629 (Jun. 1975).
Dartois, R. "Results of a phase 3, double-blind, safety and efficacy study comparing tigecycline with vancomycin/aztreonam to treat complicated skin and skin structure infections" 44th ICAAC Abstracts, American Society for Microbiology, Oct. 30-Nov. 2, 1994, Washington, D.C.; Abstr L-986, p. 389 (1994).
Ellis-Grosse, E.J. et al. "The efficacy and safety of tigecycline in the treatment of skin and skin-structure infections: results of 2 double-blind phase 3 comparison studies with vancomycin-aztreonam" Clin. Infect. Dis. 41(Suppl 5):S341-S353 (Sep. 1, 2005).
Fanning, W.L. et al. "Distressing side-effects of minocycline hydrochloride" Arch. Intern. Med. 136:761-762 (Jul. 1976).
Frampton, J.E. et al. "Tigecycline" Drugs 65(18):2623-2635 (2005).
Garrison, M.W. et al. "Tigecycline: An Investigational Gylcylcycline Antimicrobial with Activity Against Resistant Gram-Positive Organisms" Clinical Therapeutics 27:12-22 (2005).
Gennaro, A., Remington Farmacia, Edition 19a, pp. 2337, 2368 (1995).
Gump, D.W. et al. "Side effects of minocycline: different dosage regimens" Antimicrob. Agents Chemother. 12(5):642-646 (Nov. 1977).
Harris, R. et al. "Tigecycline (Tygacil): a novel first-in-class, broad-spectrum intravenous antibiotic for the treatment of serious bacterial infections" P&T 31(1):18-19,24-27,59 (2006).
Hirata, T. et al. "Effects of Efflux Transporter Genes on Susceptibility of Escherichia coli to Tigecycline (GAR-936)" Antimicrobial Agents and Chemotherapy 48:2179-2184 (2004).
Hu, M. et al. "Characterization and comparison of calcium chelation properties of minocycline and a new tetracycline analogue, glycylcycline" Pharm. Res. 11(10 Suppl.):S-272 (Oct. 1994).
Hunter, P.A. et al. "GAR-936. Tetracycline Antibiotic. Tigecycline; TBG-MINO; WAY-GAR-936" Drugs of the Future 26(9):851-858 (2001).
International Search Report for PCT/US2006/08827 dated Aug. 14, 2006.
Jul. 12, 2006 Letter from Department of Health and Human Resources to Wyeth Pharmaceuticals, Inc. (Exhibit I to Ofslager Declaration).
Jun. 15, 2005 Letter from Department of Health and Human Resources to Wyeth Pharmaceuticals, Inc. (Exhibit G to Ofslager Declaration).
King, G.L. "Animal models in the study of vomiting" Can. J. Physiol. Pharmacol. 68:260-268 (1990).
Lachman et al. The Theory and Practice of Industrial Pharmacy. Varghese Publishing House, Dadar, Bombay, 1987; pp. 672-673, 780-784.
Li, C. et al. "Quantitation of tigecycline, a novel glycycicycline, by liquid chromatography" J. Chromatog. B 811:225-229 (2004) Erratum included at the end.
Milatovic, D. et. al., "Activities of the Glycylcycline Tigecycline (GAR-936) against 1,924 Recent European Clinical Bacterial Isolates" Antimicrobial Agents and Chemotherapy 47:400-404 (2003).
Mitscher, L.A. The Chemistry of the Tetracyline Antibiotics. Grunwald, Gary L. [ed.], Marcel Dekker, Inc., New York; Chapter 6.3, p. 172-173 and Chapter 2, p. 53-54 (1978).
Muralidharan, G. et al. "Pharmacokinetics (PK), safety and tolerability of GAR-936, a novel glycylcycline antibiotic, in healthy subjects" 39th ICAAC Abstracts, American Society for Microbiology, Sep. 26-29, 1999, San Francisco, CA; Abstr. 416, p. 303 (1999).
Nathwani, D. "Tigecycline: clinical evidence and formulary positioning" Int. J. Antimicrob. Agents 25(3):185-192 (Mar. 2005).
Office Action in U.S. Appl. No. 11/455,144, mailed on Dec. 31, 2008.
Office Action in U.S. Appl. No. 11/455,144, mailed on Apr. 17, 2009.
Office Action in U.S. Appl. No. 11/455,144, mailed on Sep. 11, 2009.
Patel, R. et. al., "In Vitro Activity of GAR-936 against Vancomycin-resistant Enterococci, Methicillin-resistant Staphylococcus aureus and Penicillin-resistant Streptococcus pneumoniae" Diagnostic Microbiology and Infectious Disease 38:177-179 (2000).
Pawelczyk, E. et al. "Kinetics of drug decomposition. Part 73. Kinetics and mechanism of vitamin K3 soluble form thermal decomposition in solid phase" Pol. J. Pharmacol. Pharm. 34(5-6):399-408 (Nov.-Dec. 1982).
Pawelczyk, E. et al. "Kinetics of Drug Decomposition, Part 74. Kinetics of Degradation of Minocycline in Aqueous Solution" Polish Journal of Pharmacology and Pharmacy 34:409-421 (1982).
Petersen, P.J. et. al. "In Vitro and In Vivo Activities of Tigecycline (GAR-936), Daptomycin, and Comparative Antimicrobial Agents against Glycopeptide-Intermediate Staphylococcus aureus and Other Resistant Gram-Positive Pathogens" Antimicrobial Agents and Chemotherapy 46:2595-2601 (2002).
Petersen, P.J. et. al. "In Vitro and In Vivo Antibacterial Activities of a Novel Glycylcycline, the 9-t-Butylglycylamido Derivative of Minocycline (GAR-936)" Antimicrobial Agents and Chemotherapy 43:738-744 (1999).
Prescription Label for TYGACIL, revised Sep. 2009 (Exhibit J to Ofslager Declaration).
Rello, J. "Pharmacokinetics, pharmacodynamics, safety and tolerability of tigecycline" J. Chemother. 17(Supp. 1):12-22 (2005).
Remmers, E.G. "Some observations on the kinetics of the C.4 epimerization of tetracycline" J Pharm. Sci. 52:752-6 (Aug. 1963).
Report of Up to Thirty-Six Months Stability Data for Second Generation Tigecycline for Injection, 50 mg/vial in Flint Glass Vials (US Submission) dated Aug. 21, 2008 (Redacted, Exhibit L to Ofslager Declaration).
Report of Up to Twenty-Four Months Stability Data for Tigecycline for Injection, 50 mg/Vial in Flint Glass Vials dated Mar. 13, 2006 (Redacted, Exhibit K to Ofslager Declaration).
Schell, S. et al. "Predictors of length of intravenous antibiotic treatment and hospitalization in patients with complicated intra-abdominal infections (cIAI): findings from pooled clinical studies comparing tigecycline and imipenem/cilastatin" 45th ICAAC Abstracts, American Society for Microbiology, Dec. 16-19, 2005, Washington, D.C.; Abstr 503210 (2005).
Smith, K.L. et al. "Tigecycline" Formulary 40:245-254 (2005).
Sum, P-E. et al. "Synthesis and Structure-Activity Relationship of Novel Glycylcycline Derivatives Leading to the Discovery of GAR-936" Bioorganic & Medicinal Chemistry Letters 9:1459-1462 (1999).
Yu, H. "Freeze-Dried Powder Injection of Minocyline Hydrochloride and Its Preparation" [online] retrieved from file HCAPLUS, STN Database, Chemical Abstracts Service, Accession No. 2004:274666 (2004).
Yuen, P.H. et al., "Kinetics of Concomitant Degradation of Tetracyine to Epitetracycline, Anhydrotetracycline, and Epianhydrotetracycline in Acid Phosphate Solution" Journal of Pharmaceutical Sciences 66:1648-1650 (1977).
Zhanel, G.G. et al. "The Glycylcyclines: A Comparative Review with the Tetracyclines" Drugs 64(1):63-88 (2004).
B. Braun Medical, Inc., 0.9 Sodium Chloride Injection USP, Package Insert, downloaded from http://dailymed.nlm.nih.gov/dailymed/lookup.cfm?setid=7f22c06b-6b4d-4b49-a4b2-d2169f2bd653.
B. Braun Medical, Inc., Dextrose Injection USP, Package Insert, downloaded from http://dailymed.nlm.hih.gov/dailymed/lookup.cfm?setid=085614c7-ada4-4e2c-87c0-09bc2f18365a.
Bedu-Addo, "Understanding Lyophilization Formulation Development", Pharmaceutical Technology.
Declaration of Jennifer Brooks submitted in opposition proceedings against Pfizer's U.S. Patent No. 7,879,828 on Nov. 1, 2013.
Declaration of Christian Noble submitted in opposition proceedings against Pfizer's U.S. Patent No. 7,879,828 on Nov. 1, 2013.
Declaration of Mark L. Nelson, Ph.D.; submitted in opposition proceedings against Pfizer's U.S. Patent No. 7,879,828 on Nov. 1, 2013.
Declaration of Christian Schoenberg submitted in opposition proceedings against Pfizer's U.S. Patent No. 7,879,828 on Nov. 1, 2013.
Geneidi et al, "Tetracyclines-Vitamins Formulations Stability Screening Tests Using Differential Thermal Analysis", Sci. Pharm. 49:172-179 (1981).

(56) References Cited

OTHER PUBLICATIONS

Herman et al, "The Effect of Bulking Agent on the Solid-State Stability of Freeze-Dried Methylprednisolone Sodium Succinate", Pharmaceutical Research 11(10):1467-1473 (1994).
Kirsch et al, "Development of a Lyophilized Formulation for (R,R)-Formoterol (L)-Tartrate", Drug Development and Industrial Pharmacy 27(1):89-96 (2001).
Kreilgård, "Tetracycliners kemiske stabilitet i vandig opløsning En oversigt", Archiv for Pharmaci og Chemi 80(23):1083-1093 (1973).
Translation of Kreilgård, "Chemical stability of tetracyclines in aqueous solution—An overview".
Moreno-Cerezo et al, "A stability study of tetracycline and tetracycline cyclodextrins in tablets using a new HPLC method", Journral of Pharmaceutical and Biomedical Analysis 26:417-426 (2001).
Naggar et al, "Effect of Solubilizers on the Stability of Tetracycline", Pharmazie 29(2):126-129 (1974).
Nelson; "The chemistry and cellular biology of the tetracyclines"; Tetracyclines in Biology, Chemistry and Medicine; ed. by Nelson et al.; Birkhäuser Verlag/Switzerland; 2001 edition, pp. 3-63.
Pastia et al, "Cercetâri asupra stabilitâtii clorhidratului de tetraciclina in unele formule de unguent si de siropuri", Revista Medico-Chirurgicala 79(3):455-459 (1975).
Translation of Pastia et al, "Research on the Stability of Tetracycline Hydrochloride in Certain Ointment and Syrup Formulations".
Schneider, "Proton and metal ion binding of tetracyclines", Tetracyclines in Biology, Chemistry and Medicine; ed. by Nelson, et al.; Birkhäuser Verlag/Switzerland; 2001 edition, pp. 65-104.
Trivedi et al, "Stability Studies on Hamycin and Tetracycline Hydrochloride with Selected Diluents", Hindustan Antibiotics Bulletin 16(4):175-184 (1974).
U. S. Food and Drug Administration, Center for Drug Evaluation and Research, Clinical Pharmacology and Biopharmaceutics Review(s), Application No. 21-821 (Tygacil®) (2005).
United States Pharmacopeia, National Formulary, "Dextrose Injection", p. 218 (20th Rev. 1980).
United States Pharmacopeia, National Formulary, "Sodium Chloride Injection", pp. 727-728 (20th Rev. 1980).
USPTO, Petition for InterPartes Review, *Apotex Inc. v. Wyeth LLC*, Patent No. 7,879,828 (2013).
Cho, K.H., et al, "Development of a novel combination tablet containing trimebutine maleate and mosapride citrate for the treatment of functional dyspepsia", International Journal of Pharmaceutics, 400:145-152 (2010).
De Rizzo, E., et al, "Sorbitol-Gelatin and Glutamic Acid-Lactose Solutions for Stabilization of Reference Preparations of Measles Virus", Bulletin of the Pan American Health Organization, 23(3):299-305 (1989).
Haronikova, K., et al, "Study of stability and interactions of diclofenac in aqueous dispersions of Methocel K, lactose, maize starch and simple granulate", Farmaceuticky Obzor. 65(4):87-95 (1996) (English Abstract).
Kitamura, S., et al, "Polymorphism of mefloquine hydrochloride", International Journal of Pharmaceutics, 101(1-2):127-144 (1994).

Kovalcik, T.R., et al, "The Stability of Cyclophosphamide in Lyophilized Cakes. Part 1. Mannitol, Lactose, and Sodium Bicarbonate as Excipients", Journal of Parenteral Science & Technology, 42(1):29-37 (1988).
Orte, J.C., et al, "Kinetic study of the hydrolysis of salicylsalicylic acid in the presence of stabilizers", Dept. de Quim. Fisica, Fac. de Farm., Univ. de Granada, Granada, Spain, Farmaco Ed. Prat., 42:117-122 (1987).
Sekiya, N., et al, "Improves Stability of OPALMON® Tablets under Humid Conditions IV: Effect of Polysaccharides and Disintegrants on the Stability and Dissolution Property of OPALMON® Tablets", Chemical and Pharmaceutical Bulletin, 56(1):7-11 (2008).
U.S. Appl. No. 11/374,300, Information Disclosure Statement Under 37 C.F.R § 1.97(b) and SB/08, Sep. 6, 2007.
U.S. Appl. No. 11/374,330, Final Office Action, Apr. 5, 2010.
U.S. Appl. No. 11/374,330, Interview Summary Record, Sep. 10, 2010.
U.S. Appl. No. 11/374,330, Amendment and Response, Oct. 5, 2010.
U.S. Appl. No. 11/374,330, Declaration of Christian Ofslager under 37 C.F.R. § 1.132, Oct. 5, 2010.
Notice of Allowability in U.S. Appl. No. 11/374,330.
Wyeth V. Sandoz—Report dated Feb. 3, 2012.
Wyeth V. Sandoz—Order dated Mar. 1, 2012.
Fresenius Kabi USA, LLC., "Complaint", Nov. 13, 2013.
CFT Pharmaceuticals LLC, "Complaint", Filed Jun. 19, 2014.
Aurobindo Pharma Ltd. and Aurobindo Pharma USA, Inc., "Complaint", Filed Jul. 2, 2014.
Murphy, T.M., et al, "Therapeutic Efficacy of GAR-936, a Novel Glycylcycline, in a Rat Model of Experimental Endocarditis", Antimicrobial Agents and Chemotherapy, 44(11):3022-3027 (2000).
Zacharis, E., et al, "Volatile buffers can override the "pH memory" of subtilisin catalysis in organic media", Proc. Natl. Acad. Sci. USA, 96(4):1201-1205 (1999).
Curtis, J.R., et al, "Diseases of the urinary system; Drug-induced renal disorders: I", British Medical Journal, 242-244 (1977).
Declaration of Christian L. Ofslager, U.S. Patent 7,879,828, Case IPR2014-00115, *Apotex, Inc. v. Wyeth LLC* (Jul. 21, 2014).
Declaration of Henry Grabowski, Ph.D., U.S. Patent 7,879,828 B2, Case IPR2014-00115, *Apotex, Inc. v. Wyeth LLC* (Jul. 22, 2014).
Expert Declaration of Robert O. Williams III, Ph.D., U.S. Patent 7,879,828, Case IPR2014-00115, *Apotex, Inc. v. Wyeth LLC* (Jul. 22, 2014).
Expert Declaration of Lester A. Mitscher, Ph.D., U.S. 7,879,828, Case IPR2014-00115, *Apotex, Inc. v. Wyeth LLC* (Jul. 22, 2014).
Patent Owner Wyeth LLC's Response, U.S. Patent 7,879,828, Case IPR2014-00115, *Apotex, Inc. v. Wyeth LLC* (Jul. 22, 2014).
Petition for Inter Partes Review of U.S. Patent No. 7,879,828, Initiative for Responsibility in Drug Pricing LLC, Aug. 8, 2014, 47 Pages.
Declaration of Albert J. Berger, Ph.D., Initiative for Responsibility in *Drug Pricing, LLC v. Wyeth LLC*, U.S. Patent No. 7,879,828, Aug. 7, 2014, 93 Pages.
Barringer, W.C., et al., "Minocycline hydrochloride and its relation to other Tetracycline Antibiotics", American Journal of Pharmacy and the Sciences Supporting Public Health, 146(6):179-191 (1974) Abstract.

TIGECYCLINE COMPOSITIONS AND METHODS OF PREPARATION

This is a continuation of application Ser. No. 11/374,330, filed on Mar. 13, 2006, and to be issued as U.S. Pat. No. 7,879,828 on Feb. 1, 2011, and claims priority from and the benefit of U.S. provisional application Ser. No. 60/661,030 filed on Mar. 14, 2005, both of which are hereby incorporated by reference in their entirety.

The present invention relates to improved tigecycline compositions and methods for making such compositions. The inventive compositions have improved stability in both solid and solution states. The inventive compositions comprise tigecycline, a suitable carbohydrate, and an acid or buffer. The combination of the suitable carbohydrate and the acid or buffer reduces tigecycline degradation as explained below. The present invention provides advantages over the prior art by providing for stable tigecycline compositions and methods for making such compositions that achieve stability against both oxidative degradation and epimerization. These compositions are, therefore, more stable when dissolved, lyophilized, reconstituted, and/or diluted than compositions of tigecycline not made according to the invention.

Tigecycline is a known antibiotic in the tetracycline family and a chemical analog of minocycline. It may be used as a treatment against drug-resistant bacteria, and it has been shown to work where other antibiotics have failed. For example, it is active against methicillin-resistant *Staphylococcus aureus*, penicillin-resistant *Streptococcus pneumoniae*, vancomycin-resistant enterococci (D. J. Beidenbach et. al., Diagnostic Microbiology and Infectious Disease 40:173-177 (2001); H. W. Boucher et. al., Antimicrobial Agents & Chemotherapy 44:2225-2229 (2000); P. A. Bradford Clin. Microbiol. Newslett. 26:163-168 (2004); D. Milatovic et. al., Antimicrob. Agents Chemother. 47:400-404 (2003); R. Patel et. al., Diagnostic Microbiology and Infectious Disease 38:177-179 (2000); P. J. Petersen et. al., Antimicrob. Agents Chemother. 46:2595-2601 (2002); and P. J. Petersen et. al., Antimicrob. Agents Chemother. 43:738-744 (1999), and against organisms carrying either of the two major forms of tetracycline resistance: efflux and ribosomal protection (C. Betriu et. al., Antimicrob. Agents Chemother. 48:323-325 (2004); T. Hirata et. al. Antimicrob. Agents Chemother. 48:2179-2184 (2004); and P. J. Petersen et. al., Antimicrob. Agents Chemother. 43:738-744 (1999).

Tigecycline has historically been administered intravenously because it exhibits generally poor bioavailability when given orally. Intravenous solutions have largely been prepared immediately prior to use, e.g., administration to a patient, from lyophilized powders because tigecycline degrades in solution principally via oxidation. It would be preferable as well as desirable to have an intravenous formulation of tigecycline that did not require immediate use and could remain stable in solution for up to 24 hours.

Tigecycline is currently manufactured as a lyophilized powder. Due to the propensity for tigecycline to degrade, these powders are prepared under low-oxygen and low-temperature conditions in order to minimize degradation. Such processing is expensive because it requires special equipment and handling.

The typical process for preparing these powder compositions involves dissolving tigecycline in water (compounding) and lyophilizing (freeze-drying) the solution to dryness to form solid cakes of amorphous tigecycline. These cakes are then loaded under nitrogen into stoppered glass vials and shipped to end users such as hospital pharmacies. Prior to being administered to patients, the cakes are reconstituted, often in 0.9% saline, to a concentration of, for example, about 10 mg/mL. At this concentration, tigecycline degrades rapidly in solution and therefore, must be used without delay. Thus, these reconstituted solutions are immediately diluted (also known as admixing) to about 1 mg/mL with saline or other pharmaceutically acceptable diluents into intravenous bags for patient delivery.

In this diluted state, tigecycline is ready for intravenous delivery to a patient. At a concentration of 1 mg/mL, however, tigecycline should be used within 6 hours of dilution. Because intravenous infusions may take several hours, hospital personnel must act quickly so that from the time admixture begins to the time the tigecycline dose has been administered to a patient, not more then 6 hours have elapsed. It would be more preferred to provide hospital staff with the flexibility and advantages that come with longer admixture and reconstitution times so that, for instance, a hospital pharmacist could prepare a solution the day before it is needed to be administered to a patient.

Tigecycline has such a short admixture time and the reconstitution time is essentially zero because in solution, tigecycline oxidation is relatively rapid. Under current manufacturing, storage, and administration conditions, the most prevalent form of degradation is via oxidation. The reason oxidation is the most prevalent form of degradation in previous formulations relates to the chemical structure of tigecycline. It possesses a phenol moiety, and it is well known in the art of organic chemistry that phenols are particularly prone to oxidation. When tigecycline is dissolved in water prior to lyophilization, the pH is slightly basic (about 7.8). This is higher than the pKa of the phenolic group on tigecycline. Thus, in both water and saline solutions, the phenolic group becomes deprotonated and more susceptible to reaction with oxygen which is why tigecycline compounding and lyophilization occur under a nitrogen blanket. Accordingly, care to avoid unnecessary exposure to oxygen must be taken by hospital staff during reconstitution and dilution.

If the pH of the tigecycline solution were less than the pKa of the phenolic group on tigecycline, then oxidation would occur, but to a lesser extent. Indeed, it has been observed that tigecycline oxidative degradation does decrease when the pH is lowered. At low pH, however, another degradative process occurs, epimerization. At lower pHs, epimerization emerges as the most predominant degradation pathway.

Tigecycline differs structurally from its epimer in only one respect.

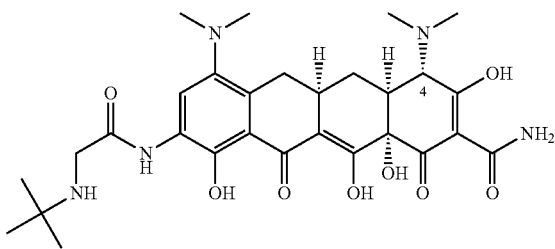

FORMULA I

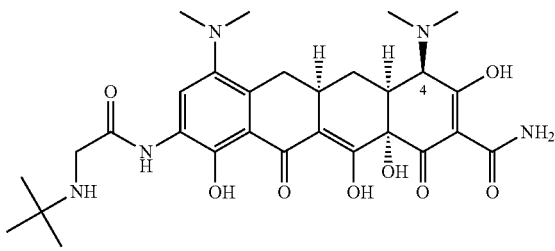

FORMULA II

In tigecycline, the N-dimethyl group at the 4 carbon is cis to the adjacent hydrogen as shown above in formula I, whereas in the epimer, formula II, they are trans to one another in the manner indicated. Although the tigecycline epimer is believed to be non-toxic, it lacks the anti-bacterial efficacy of tigecycline and is, therefore, an undesirable degradation product.

In the lyophilized state, tigecycline follows the same degradation pathways as in solution, but the rate of degradation is slower. Thus, when tigecycline is lyophilized in water such that the pH is about 7.8, the resulting lyophilized cake exhibits oxidative degradation, albeit at a slower rate than in solution. Similarly, when tigecycline is lyophilized in an acidic solution, the primary degradation pathway is epimerization and it also occurs at a slower rate than in solution.

Epimerization is a known degradation pathway in tetracyclines generally, although the rate of degradation may vary depending upon the tetracycline. Comparatively, the epimerization rate of tigecycline is particularly fast. The tetracycline literature reports several methods scientists have used to try and minimize epimer formation in tetracyclines. In some methods, the formation of calcium, magnesium, zinc or aluminum metal salts with tetracyclines limit epimer formation when done at basic pHs in non-aqueous solutions. (Gordon, P. N, Stephens Jr, C. R., Noseworthy, M. M., Teare, F. W., U.K. Patent No. 901,107). In other methods, (Tobkes, U.S. Pat. No. 4,038,315) the formation of a metal complex is performed at acidic pH and a stable solid form of the drug is subsequently prepared.

Other methods for reducing epimer formation include maintaining pHs of greater than about 6.0 during processing; avoiding contact with conjugates of weak acids such as formates, acetates, phosphates, or boronates; and avoiding contact with moisture including water-based solutions. With regard to moisture protection, Noseworthy and Spiegel (U.S. Pat. No. 3,026,248) and Nash and Haeger, (U.S. Pat. No. 3,219,529) have proposed formulating tetracycline analogs in non-aqueous vehicles to improve drug stability. However, most of the vehicles included in these inventions are more appropriate for topical than parenteral use. Tetracycline epimerization is also known to be temperature dependent so production and storage of tetracyclines at low temperatures can also reduce the rate of epimer formation (Yuen, P. H., Sokoloski, T. D., J. Pharm. Sci. 66: 1648-1650, 1977; Pawelczyk, E., Matlak, J, Pol. J. Pharmacol. Pharm. 34: 409-421, 1982). Several of these methods have been attempted with tigecycline but none have succeeded in reducing both epimer formation and oxidative degradation while not introducing additional degradants. Metal complexation, for example, was found to have little effect on either epimer formation or degradation generally at basic pH.

Although the use of phosphate, acetate, and citrate buffers improve solution state stability, they seem to accelerate degradation of tigecycline in the lyophilized state. Even without a buffer, however, epimerization is a more serious problem with tigecycline than with other tetracyclines such as minocycline.

Others of these methods similarly failed to reduce both epimerization and oxidative degradation. Although it was found that maintaining a pH of greater than about 6.0 helps reduce epimer formation, as noted above, such conditions lead to greater oxygen sensitivity. With respect to non-aqueous vehicles, although water is known to accelerate tigecycline degradation, it would be impractical to prepare an intravenous medication using such vehicles.

Whereas it has been determined that processing at temperatures lower than room temperature, such as below about 10° C., reduces the tigecycline degradation rate, such processing is expensive and it would be advantageous to use a composition that did not require expensive refrigeration during processing.

Chinese patent application CN 1390550A discloses that minocycline could be combined with an acid to increase the stability toward the oxidative degradation. It further discloses the use of a caking agent, such as mannitol. This reference says nothing about tigecycline nor does it suggest that carbohydrates could be used to reduce either oxidation or epimerization for minocycline in reduced pH environments. Indeed, minocycline can be formulated as a hydrochloride salt in intravenous products without significant epimerization. In tigecycline hydrochloride salts, however, significant epimerization occurs. Thus, minocycline and tigecycline possess different epimerization properties.

In another experiment, minocycline was lyophilized at a pH of about 5.0 and the lyophilized cake was stored for 20 days at 40° C. and 75% relative humidity. At the end of the 20 days, the cake was analyzed by HPLC. The epimer of minocycline was measured to be present at a level of 2.65% by mass. By comparison, when tigecycline was lyophilized at a pH of about 5.0 and the sample stored under the same conditions, but for only 4 days followed by HPLC analysis, the tigecycline epimer was measured to be at a level of 5.40%, over twice as much even though tigecycline was only stressed for $\frac{1}{5}^{th}$ as long as minocycline. Thus, tigecycline epimerizes much more readily than minocycline, and epimerization is a much more significant problem with tigecycline than it is for minocycline.

The present invention addresses the various problems and disadvantages of the prior art by providing for stable compositions of tigecycline in solid and solution form. By lyophilizing an aqueous solution containing tigecycline and a suitable carbohydrate at an acidic pH, we have prepared tigecycline compositions that are more stable against both oxidative degradation and epimerization than existing compositions. Because the pH is acidic, oxidative degradation has been minimized. Furthermore, it has been determined that suitable carbohydrates act to stabilize tigecycline against epimer formation at acidic pHs.

Compositions of the invention are more stable in the lyophilized state than the existing compositions and do not require low-temperature or low-oxygen processing conditions. Such compositions are also expected to possess reconstitution and admixture stability times greater than that of the existing compositions. For example, one embodiment of the invention is stable for 6 hours after reconstitution and stable for an additional 18 hours after admixture. These extended stability times make tigecycline much easier to use in a hospital environment by providing needed flexibility to hospital staff when treating patients.

Solid-state compositions of the invention comprise tigecycline, a suitable carbohydrate, and an acid or buffer.

Suitable carbohydrates are those carbohydrates capable of reducing epimer formation in at least one solid form prepared in at least one pH environment when compared to a tigecycline solid form prepared at the same pH environment lacking suitable carbohydrates. In one embodiment, the pH environment ranges from about 3.0 to about 7.0, such as pHs ranging from about 4.0 to about 5.0, or from about 4.2 to about 4.8. In one embodiment, the at least one solid form is chosen from powders and lyophilized cakes of tigecycline. Examples of suitable carbohydrates include the anhydrous, hydrated, and solvated forms of compounds such as lactose, mannose, sucrose, and glucose. Suitable carbohydrates include mono and disaccharides e.g. an aldose monosaccharide or a disaccharide, preferably a disaccharide such as lactose and sucrose. Lactose is most preferred. Accordingly, suitable carbohydrates may include different solid forms. For example, by lactose we include the different solid forms of lactose such as anhydrous lactose, lactose monohydrate or any other hydrated or solvated form of lactose. Lactose and sucrose are disaccharides. It is therefore expected that disaccharides as a class will work according to the invention.

The compositions of the invention include solutions, such as those prepared prior to lyophilization, containing tigecycline, a suitable carbohydrate, and an acid or buffer. In some embodiments of the invention, the solutions may be stored for several hours prior to lyophilization in order to provide greater manufacturing flexibility. Compositions of the invention further include lyophilized powders or cakes containing tigecycline, a suitable carbohydrate, and an acid or buffer.

In some embodiments of the invention, the suitable carbohydrate used is lactose monohydrate and the molar ratio of tigecycline to lactose monohydrate in the lyophilized powder or cake is between about 1:0.2 to about 1:5. Some embodiments have tigecycline to lactose monohydrate molar ratios of between about 1:1.6 to about 1:3.3.

Compositions of the invention also include solutions made from the lyophilized powder or cake by, for example, reconstitution with saline or other pharmaceutically acceptable diluents. Compositions of the invention further include solutions resulting from diluting those reconstituted solutions with pharmaceutically acceptable diluents for use in intravenous bags.

Any carbohydrate capable of reducing epimer formation in the invention is a suitable carbohydrate and this invention is not limited to compositions employing those carbohydrates specifically identified.

It is expected that derivatives of sugars, for example, may work according to the invention to reduce epimer formation. Thus, to the extent that derivatives of sugars, such as sugar alcohols, glucoseamines, and alkyl esters alone or in combination reduce epimer formation according to the invention, they are suitable carbohydrates. Likewise, other suitable carbohydrates may include higher saccharides such as polysaccharides; complex carbohydrates such as hetastarch, dextran; and celluloses such as hydroxypropylmethyl cellulose and hydroxypropyl cellulose. It is further expected that combinations of carbohydrates, including monosaccharides and trisaccharides, will be suitable carbohydrates and work to reduce epimer formation according to the invention.

Acids and buffers of the invention include any pharmaceutically acceptable acid or buffer capable of adjusting the pH of a tigecycline/suitable carbohydrate solution to between about 3.0 to about 7.0, about 4.0 to about 5.0, or about 4.2 to about 4.8. Examples of such acids include, but are not limited to, hydrochloric acid, including 1.0 N HCl, gentisic acid, lactic acid, citric acid, acetic acid, and phosphoric acid. Examples of suitable buffers include succinates.

Compounds of the invention may be prepared via a number of acceptable methods. The methods described below are exemplary and not meant to limit the invention.

In one method of the invention, tigecycline is dissolved in water to form a solution. The pH of the solution is subsequently lowered by addition of an acid or buffer. A suitable carbohydrate is then dissolved in the solution and the solution is lyophilized to dryness to form a lyophilized powder or cake.

Tigecycline may be blended with a suitable carbohydrate and dissolved in water. After the pH of the solution is adjusted so that it is acidic, the solution may then be lyophilized to dryness to form a lyophilized powder or cake.

Lyophilization of solutions of the invention may be accomplished by any pharmaceutically acceptable means. Once lyophilized, compositions of the invention may be stored under an inert gas, such as nitrogen, to further slow the degradation process, but, unlike the current tigecycline composition, such low oxygen environments are not necessary for the invention.

When tigecycline is combined with a suitable carbohydrate, any solid-state form of tigecycline that is sufficiently soluble in water may be used. Such solid-state forms include crystalline tigecycline polymorphs, amorphous forms, and salts.

Additionally, when preparing tigecycline solutions of the invention for lyophilization, one adds sufficient acid or buffer to the aqueous solution containing tigecycline to obtain a pH from about 3.0 and about 7.0 including from about 4.0 to about 5.0 and from about 4.2 to about 4.8.

The compositions of the invention may be prepared for single-dosage use. In this embodiment, the solutions of the invention are lyophilized in individual vials, such as 20 ml vials. Upon lyophilization, the vials are stoppered with any pharmaceutically acceptable stopper. The stoppered vials are then shipped for use.

When needed, the vials can be reconstituted by adding sufficient diluent to achieve the desired concentration of tigecycline. The concentration of reconstituted solutions may be easily determined by those of ordinary skilled in the art. Any pharmaceutically acceptable diluent may be used. Examples of such diluents include water, saline, such as 0.9% saline, Lactated Ringer's Injection solution and dextrose solutions including 5% dextrose (D5W).

Reconstituted solutions of the invention may then be stored in a reconstituted state, unlike current compositions, prior to admixture. Admixture can occur, for example, in an intravenous bag. To prepare an admixture, sufficient reconstituted solution is mixed in an intravenous bag containing a pharmaceutically acceptable diluent such as saline solution or dextrose solution such as D5W. The concentration of admixtures may be easily determined by those of ordinary skill in the art. Admixture times for compositions of the invention can be much longer than those of the existing composition. Once admixed, the tigecycline solution is ready for patient administration. The admixture may be administered alone or together with another pharmaceutical agent or composition.

The following six examples illustrate various embodiments of the invention and are not intended to limit the invention in any way. Each example details several experiments where tigecycline was dissolved with a carbohydrate in aqueous acidic solution, lyophilized, and analyzed for degradation products by HPLC. The HPLC conditions for each example were essentially the same. The tables accompanying the examples reflect the results of the HPLC data which show the oxidative degradation products identified in the tables as relative retention times (RRT) 0.50/MW 601 and RRT 0.55/MW 583, the epimer (RRT 0.74/MW 585), and the total amount of tigecycline present under a variety of conditions (identified as "Tigecycline" in the tables"). In many instances, after the solutions were lyophilized, they were placed under accelerated stability conditions of 40° C. and 75% relative humidity. These conditions are industry standards used for simulating the effect of long-term storage under normal shelf conditions.

In example 1, solutions of tigecycline, lactose, and 1.0 N HCl were lyophilized and the resulting cakes were placed in stability chambers at 40° C. and 75% relative humidity for 25 days. At the end of the 25 days, the cakes were analyzed by HPLC to identify degradation products.

A similar experiment is detailed in Example 2a. There, the lyophilized cakes were analyzed by HPLC after being stored for 39 days at 40° C. and 75% relative humidity. Sample cakes from two of the experiments were reconstituted in D5W (5% dextrose) and samples from the remaining cakes were reconstituted in saline immediately prior to HPLC analysis.

In experiment 2b, after the lyophilized cakes were stressed as per the conditions in example 2a, several of the cakes were reconstituted in 0.9% saline and kept in solution for 6 hours. Others were reconstituted in dextrose. At the end of the 6 hour period, some of these solution samples, as identified in table 2b, were tested by HPLC.

Example 2c illustrates a stability test on admixed solutions. In these solutions, the reconstituted solutions of example 2b were held for 6 hours at about 10 mg/mL and then diluted to about 1 mg/mL, the typical intravenous concentration for tigecycline, and held for 18 hours prior to analysis by HPLC (table 2c).

In example 3, gentisic acid, rather than hydrochloric acid, was used to reduce the pH of the pre-lyophilized solutions of tigecycline. Once lyophilized, the cakes were stressed at 45° C. and 75% relative humidity for 48 days and then analyzed by HPLC.

The samples of example 4 show the effects of changing from lactose to other carbohydrates on epimer formation and tigecycline recovery when making the pre-lyophilized tigecycline solutions. In each of examples 4a, 4b, and 4c, the indicated solutions were prepared and lyophilized. Each cake was stressed according to the parameters provided in examples 4a-4c, taken into solution, and analyzed by HPLC.

Hold time, the time in between compounding and lyophilization, and order of tigecycline and lactose addition were studied as factors in epimer formation and tigecycline recovery in example 5. Once the cakes were lyophilized, they were stressed at 40° C. and 75% relative humidity for 48 days prior to HPLC analysis. Summaries of the HPLC data appear in table 5.

The ratio of lactose to tigecycline was varied in the experiments in example 6. When preparing the solutions to be lyophilized, varying ratios of lactose to tigecycline were employed. The mass ratios are reported in the first column of table 6. The solutions, which each had a pH of about 5.0, were subsequently lyophilized to dryness and the resulting cakes were stressed at 40° C. and 75% relative humidity for 20 days and analyzed by HPLC.

EXAMPLE 1

Tigecycline (1880 mg) was dissolved in 75 ml of Milli-Q water to form a bulk solution. An aliquot from this bulk solution containing approximately 100 mg of tigecycline was dissolved into a 20 ml vial containing 200 mg of lactose monohydrate. Another aliquot of the bulk solution containing approximately 100 mg of tigecycline was placed into an empty 20 ml sample vial. No pH adjustment was made to either of these two solutions. The solutions were subsequently lyophilized to dryness.

The pH of the remaining bulk solution was lowered to about 6.0 with the addition of 1.0N HCl. Once a pH of about 6.0 was obtained, an aliquot from the bulk solution containing about 100 mg of tigecycline was dissolved into a 20 ml sample vial containing about 200 mg of lactose monohydrate and the resulting solution was lyophilized to dryness. The remaining bulk solution was treated with 1.0N HCl until a pH of about 5.5 was obtained at which point 100 mg of tigecycline from the bulk solution was transferred into a 20 ml vial containing 200 mg of lactose monohydrate. After dissolution, the solution was lyophilized to dryness. Similarly, 20 ml sample vials containing solutions of about 100 mg of tigecycline and about 200 mg of lactose were prepared at pHs of about 5.0 and about 4.5. Another solution sample was prepared at about pH 4.5 without any lactose. In each case, the solutions were subsequently lyophilized to dryness. All lyophilizations were done on solutions frozen at −70° C. by dry ice with acetone.

The lyophilized samples were placed in a 40° C./75% RH chamber for 25 days. Afterwards, the samples were analyzed by HPLC and a summary of the results appears below in table 1, which reflects the major degradation products for each cake that was tested. The sum total of the 6 major degradation products listed in the tables does not equal 100% because not all degradation products are listed in the table. Of the 7 cakes tested in example 1, 5 were compositions of the invention and the first two (tigecycline alone without pH adjustment and tigecycline plus lactose without pH adjustment) were controls.

The advantages of the compositions of the invention are apparent from this example. For instance, in the composition prepared without lactose at a pH of about 4.5, only 74.10% tigecycline was detected whereas the epimer was present in an amount of 23.51%. By comparison, the pH 4.5 sample with lactose contained only 2.53% epimer and had a tigecycline content of 97.17%.

TABLE 1

| | RRT | | | | | |
|---|---|---|---|---|---|---|
| | 0.5 | 0.55 | Epimer 0.74 | 1.25 MW | 1.67 | Tigecycline |
| Sample ID | 601 | 583 | 585 | 528 | 556 | 585 |
| Tigecycline only (no pH adjustment) | 0.57 | 2.15 | 6.50 | 2.50 | 1.72 | 80.59 |
| Tigecycline + lactose (no pH adjustment) | 0.61 | 0.48 | 1.05 | 0.71 | 1.05 | 91.95 |
| pH 6.0 + lactose | 0.04 | 0.15 | 2.56 | 0.04 | 0.12 | 96.83 |
| pH 5.5 + lactose | 0.01 | 0.11 | 2.54 | 0.01 | 0.04 | 97.07 |
| pH 5.0 + lactose | 0.01 | 0.04 | 2.43 | ND | 0.02 | 97.27 |
| pH 4.5 (no lactose) | 0.11 | 0.21 | 23.51 | 0.14 | 0.16 | 74.10 |
| pH 4.5 + lactose | 0.01 | 0.05 | 2.53 | ND | 0.01 | 97.17 |

ND = Not detected;
MW is molecular weight;
RRT means relative retention time to tigecycline peak.

EXAMPLE 2

2a. Tigecycline (1700 mg) was dissolved in 85 ml of Milli-Q water to form a bulk solution. Solutions containing about 100 mg of tigecycline and about 200 mg of lactose monohydrate were prepared at pHs of about 5.2, 5.0, 4.8, and 3.0 in the same manner that tigecycline/lactose/HCl solutions were prepared in example 1. A solution of tigecycline and lactose at pH of about 4.5 was prepared by adding 1.0 N NaOH to the bulk solution at pH 3.0 followed by dissolving an aliquot of bulk solution containing about 100 mg of tigecycline into a 20 ml vial containing about 200 mg of lactose monohydrate. All samples were lyophilized (frozen at −50° C. by freeze dryers from AdVantage/Virtis) to dryness. The lyophilized samples were placed in a 40° C./75% RH chamber for 39 days and sub-sampled and analyzed by HPLC. The data are shown in table 2a.

2b. At the end of 39 days, the lyophilized cakes of Example 2a were reconstituted with 0.9% NaCl to a concentration of 10 mg/ml of tigecycline and kept at room temperature for 6 hours. Separate aliquots of the solutions at pH of about 5.0 and about 4.5 were reconstituted with 5% Dextrose, instead of saline, to a concentration of about 10 mg/ml and kept at room temperature for 6 hours. Each of the solutions was then analyzed by HPLC, and the results are shown in Table 2b.

The data show that the compositions of the invention protect against epimer formation in reconstituted solutions for 6 hours. Indeed, the maximum epimer content of any one of these examples was only 2.45%, whereas the minimum tigecycline content was 97.1%. In one embodiment, where the pH was about 4.5 and the diluent was saline, at the end of the 6 hour reconstitution period, only 1.60% of epimer was present. In that embodiment, the amount of tigecycline was measured to be 98.15%, which, in some applications, may be of sufficient purity for hospital use.

2c. Admixture solutions of tigecycline (at 1 mg/ml) were made by diluting the reconstituted solution (from example 2b) with 0.9% NaCl or 5% Dextrose depending upon which diluent was used for reconstitution. The solutions were then kept at room temperature for 18 hours and analyzed by HPLC. The results are summarized in Table 2c.

The sample at about pH 4.5 with lactose and without dextrose had its epimer concentration increase from 1.60% to only 1.80% on going from reconstitution to admixture whereas the overall tigecycline content decreased only slightly for that sample from 98.15% to 97.97%. These results on the about pH 4.5 sample illustrate that that sample is sufficiently stable after the lyophilized cake is stored under accelerated stability conditions for 39 days followed by 6 hours of reconstitution and 18 hours of admixture.

TABLE 2a

| | RRT | | | | | |
|---|---|---|---|---|---|---|
| | 0.5 | 0.55 | Epimer 0.74 | 1.25 MW | 1.67 | Tigecycline |
| Sample ID | 601 | 583 | 585 | 528 | 556 | 585 |
| pH 5.2 + lactose | 0.01 | 0.08 | 2.21 | ND | ND | 97.58 |
| pH 5.0 + lactose | 0.01 | 0.07 | 2.20 | ND | 0.01 | 97.57 |
| pH 5.0 + lactose in 5% dextrose | 0.01 | 0.08 | 2.21 | ND | 0.01 | 97.38 |
| pH 4.8 + lactose | 0.01 | 0.02 | 2.15 | ND | ND | 97.63 |
| pH 4.5 + lactose | 0.01 | 0.03 | 1.37 | ND | 0.01 | 98.42 |
| pH 4.5 + lactose in 5% dextrose | 0.01 | 0.02 | 1.35 | ND | ND | 98.23 |
| pH 3.0 + lactose | 0.01 | 0.02 | 1.34 | ND | ND | 98.49 |

TABLE 2b

| | RRT | | | | | |
|---|---|---|---|---|---|---|
| | 0.5 | 0.55 | Epimer 0.74 | 1.25 MW | 1.67 | Tigecycline |
| Sample ID | 601 | 583 | 585 | 528 | 556 | 585 |
| pH 5.2 + lactose | 0.01 | 0.12 | 2.31 | 0.01 | 0.04 | 97.37 |
| pH 5.0 + lactose | 0.01 | 0.10 | 2.37 | ND | 0.03 | 97.33 |
| pH 5.0 + lactose in 5% dextrose | 0.01 | 0.10 | 2.45 | 0.01 | 0.03 | 97.10 |
| pH 4.8 + lactose | 0.01 | 0.09 | 2.32 | ND | 0.02 | 97.41 |
| pH 4.5 + lactose | 0.01 | 0.09 | 1.60 | 0.01 | 0.02 | 98.15 |
| pH 4.5 + lactose in 5% dextrose | 0.01 | 0.08 | 1.65 | ND | 0.01 | 97.96 |
| pH 3.0 + lactose | 0.01 | 0.06 | 2.10 | ND | ND | 97.70 |

TABLE 2c

| | RRT | | | | | |
|---|---|---|---|---|---|---|
| | 0.5 | 0.55 | Epimer 0.74 | 1.25 MW | 1.67 | Tigecycline |
| Sample ID | 601 | 583 | 585 | 528 | 556 | 585 |
| pH 5.2 + lactose | 0.01 | 0.05 | 2.49 | 0.01 | 0.09 | 97.11 |
| pH 5.0 + lactose | 0.01 | 0.06 | 2.57 | 0.01 | 0.06 | 97.09 |
| pH 5.0 + lactose in 5% dextrose | 0.02 | 0.05 | 2.80 | 0.01 | 0.06 | 96.66 |
| pH 4.8 + lactose | 0.02 | 0.04 | 2.52 | 0.01 | 0.04 | 97.19 |
| pH 4.5 + lactose | 0.01 | 0.03 | 1.80 | ND | 0.03 | 97.97 |
| pH 4.5 + lactose in 5% dextrose | 0.02 | 0.02 | 2.02 | ND | 0.02 | 97.56 |
| pH 3.0 + lactose | 0.01 | 0.04 | 2.72 | ND | ND | 97.13 |

EXAMPLE 3

Tigecycline (700 mg) was dissolved in 28 ml of Milli-Q water to form a bulk solution. An aliquot of the bulk solution containing about 100 mg of tigecycline was loaded into a 20 ml vial as control sample. Solution samples of tigecycline, lactose, and an acid were prepared at pHs of about 5.8, 5.1, and 4.5 according to the methods of example 1 except that gentisic acid was used to lower the pH of the bulk solution rather than 1.0 N HCl. An additional two samples of tigecycline solutions without lactose were prepared, one at a pH of about 5.1 and another at a pH of about 4.5. All of the solutions were frozen at −70° C. (by dry ice with acetone) and lyophilized to dryness. The lyophilized samples were placed in a 40° C./75% RH chamber for 48 days and analyzed by HPLC. The data are summarized in Table 3 and show that this composition works according to the invention to reduce degradation.

TABLE 3

| | RRT | | | | | |
|---|---|---|---|---|---|---|
| | 0.5 | 0.55 | Epimer 0.74 | 1.25 MW | 1.67 | Tigecycline |
| Sample ID | 601 | 583 | 585 | 528 | 556 | 585 |
| Control | 0.37 | 2.17 | 7.37 | 1.50 | 1.47 | 81.13 |
| pH 4.5 no lactose | 0.02 | 0.05 | 28.11 | 0.04 | 0.02 | 71.37 |
| pH 4.5 + lactose | 0.01 | 0.02 | 6.32 | ND | ND | 93.42 |
| pH 5.1 no lactose | 0.05 | 0.10 | 20.90 | 0.10 | 0.08 | 77.87 |
| pH 5.1 + lactose | 0.01 | 0.02 | 3.94 | ND | 0.02 | 95.82 |
| pH 5.8 no lactose | 0.04 | 0.13 | 17.38 | 0.21 | 0.21 | 81.31 |

EXAMPLE 4

4a. Tigecycline (1600 mg) was dissolved in 64 ml of Milli-Q water to form a bulk solution and two samples from the solution, each containing about 100 mg of tigecycline, were loaded into two separate sample 20 ml sample vials containing 160 mg of lactose monohydrate and 160 mg mannitol respectively. A third sample containing about 100 mg of tigecycline from the bulk solution was loaded into a blank 20 ml vial. The pH of the remainder of the bulk solution was sequentially adjusted with 1.0N HCl to about 7.0, 6.5, and 6.0 as per the procedure outlined in example 1. Sample solutions each containing about 100 mg tigecycline were loaded into 20 ml vials containing 160 mg of lactose monohydrate, 160 mg of mannitol, or neither at each pH value. The resulting solutions were lyophilized (frozen at −70° C. by dry ice with acetone) to dryness. The lyophilized samples were placed in a 40° C. oven for 70 hours and then analyzed by HPLC. The data are summarized in table 4a.

4b. Tigecycline (1800 mg) was dissolved in 72 ml of Milli-Q water to form a bulk solution. Aliquots from the bulk solution containing about 100 mg of tigecycline were loaded into three separate 20 ml vials containing about 200 mg of lactose monohydrate, fructose, and sucrose respectively. The pH of the bulk solution was sequentially adjusted with 1.0N HCl to about 6.0 and 5.4 according to the procedure outlined in example 1. At each pH value, aliquots of solution containing about 100 mg of tigecycline were taken into 20 ml vials containing 200 mg of one of the following carbohydrates:

lactose monohydrate, fructose, or sucrose and dissolved. Solutions without carbohydrates were also prepared at each pH value. The solutions were lyophilized (frozen at −70° C. by dry ice with acetone) to dryness. The lyophilized samples were placed in a 40° C. oven for 89 hours and analyzed by HPLC. The results are summarized in Table 4b.

4c. Tigecycline (1000 mg) was dissolved in 50 ml of Milli-Q water to form a bulk solution. The pH of the bulk solution was adjusted with 1.0N HCl to about 5.0. Four aliquots of bulk solution, each containing about 100 mg of tigecycline, were loaded into 20 ml vials containing about 200 mg of glucose, mannose, ribose, and xylose respectively and dissolved. A fifth aliquot of bulk solution containing about 100 mg of tigecycline was loaded into a 20 ml vial containing about 125 mg of threose and dissolved. All five solutions were lyophilized (frozen at −50° C. by freeze dryers from AdVantage/Virtis) to dryness. The lyophilized samples were placed in a 25° C./60% RH chamber for 42 days and analyzed by HPLC. The results are summarized in table 4c. Data in tables 4a-4c are meant to illustrate the effect of suitable carbohydrates such as lactose on the invention.

TABLE 4a

| | RRT | | | | | |
|---|---|---|---|---|---|---|
| | 0.5 | 0.55 | Epimer 0.74 | 1.25 MW | 1.67 | Tigecycline |
| Sample ID | 601 | 583 | 585 | 528 | 556 | 585 |
| Tigecycline only | 0.03 | 0.07 | 1.08 | ND | 0.07 | 98.51 |
| pH 7.0 | 0.03 | 0.06 | 1.15 | 0.02 | 0.09 | 98.35 |
| pH 6.5 | 0.03 | 0.06 | 1.73 | 0.02 | 0.09 | 97.78 |
| pH 6.0 | 0.02 | 0.06 | 2.69 | 0.02 | 0.08 | 96.82 |
| Tigecycline + lactose | 0.03 | 0.10 | 0.89 | ND | 0.07 | 98.33 |
| pH 7.0 + lactose | 0.03 | 0.08 | 0.94 | ND | 0.06 | 98.45 |
| pH 6.5 + lactose | 0.02 | 0.05 | 0.91 | ND | NA | 98.50 |
| pH 6.0 + lactose | ND | 0.04 | 0.90 | ND | NA | 98.54 |
| Tigecycline + mannitol | 0.05 | 0.13 | 1.40 | ND | 0.14 | 97.69 |
| pH 7.0 + mannitol | 0.05 | 0.11 | 1.80 | ND | 0.12 | 97.45 |
| pH 6.5 + mannitol | 0.03 | 0.08 | 2.28 | ND | 0.08 | 96.98 |
| pH 6.0 + mannitol | 0.02 | 0.06 | 2.56 | ND | 0.07 | 96.82 |

TABLE 4b

| | RRT | | | | | |
|---|---|---|---|---|---|---|
| | 0.5 | 0.55 | Epimer 0.74 | 1.25 MW | 1.67 | Tigecycline |
| Sample ID | 601 | 583 | 585 | 528 | 556 | 585 |
| Tigecycline only | 0.04 | 0.12 | 1.06 | 0.04 | 0.12 | 98.39 |
| pH 6.0 | 0.03 | 0.09 | 2.72 | 0.03 | 0.08 | 96.90 |
| pH 6.0 + lactose | 0.01 | 0.04 | 0.97 | ND | 0.03 | 98.76 |
| pH 5.4 + lactose | 0.01 | 0.06 | 1.01 | 0.01 | 0.03 | 98.71 |
| pH 6.0 + fructose | 0.04 | 0.09 | 17.70 | 0.02 | 0.02 | 81.92 |
| pH 6.0 + sucrose | 0.01 | 0.08 | 1.38 | 0.02 | 0.03 | 98.32 |

TABLE 4c

| | RRT | | | | | |
|---|---|---|---|---|---|---|
| | 0.5 | 0.55 | Epimer 0.74 | 1.25 MW | 1.67 | Tigecycline |
| Sample ID | 601 | 583 | 585 | 528 | 556 | 585 |
| pH 5.0 + glucose | 0.01 | 0.06 | 1.02 | ND | 0.01 | 98.81 |
| pH 5.0 + mannose | 0.01 | 0.06 | 1.23 | ND | ND | 98.60 |
| pH 5.0 + ribose | 0.44 | 0.02 | 33.30 | ND | 0.01 | 65.94 |
| pH 5.0 + xylose | 0.02 | 0.09 | 18.05 | ND | ND | 81.68 |
| pH 5.0 + threose | 0.91 | 3.41 | 7.00 | 0.07 | 0.79 | 22.85 |

EXAMPLE 5

5a. Tigecycline (1000 mg) was dissolved in 40 ml of Milli-Q water to form a bulk solution. The pH of the bulk solution was adjusted with 1.0N HCl to about 5.0. At that pH, two aliquots of the bulk solution, each containing about 100 mg tigecycline, were loaded separately into two 20 ml vials each containing about 200 mg lactose monohydrate. One sample was frozen immediately at −70° C. (by dry ice with acetone), and the other sample was kept at room temperature for 5 hours before freezing. Frozen samples were subsequently lyophilized to dryness. The lyophilized samples were placed in a 40° C./75% RH chamber for 48 days and analyzed by HPLC. The results are summarized in Table 5 as the "A" samples.

5b. Lactose monohydrate (750 mg) was dissolved in 15 ml of Milli-Q water. Tigecycline (375 mg) was added to this solution and the pH was adjusted to about 5.0 with 1.0N HCl. At this pH, two aliquots from the solution, each containing about 100 mg of tigecycline and about 200 mg of lactose monohydrate, were loaded into two 20 ml vials respectively. The solution in one sample vial was frozen immediately at −70° C. (by dry ice with acetone). The solution in the other sample was kept at room temperature for 5 hours before freezing. Frozen samples were lyophilized to dryness. The lyophilized samples were placed in a 40° C./75% RH chamber for 48 days and analyzed by HPLC. The results are summarized in Table 5 as the "B" samples. The "A" and "B" data illustrate compositions of the invention reducing degradation products.

TABLE 5

| Sample ID | RRT | | | | | Tigecycline |
|---|---|---|---|---|---|---|
| | 0.5 | 0.55 | Epimer 0.74 | 1.25 MW | 1.67 | |
| | 601 | 583 | 585 | 528 | 556 | 585 |
| A (lactose dissolved in tigecycline) | 0.01 | 0.02 | 3.18 | 0.01 | 0.02 | 96.57 |
| B (tigecycline dissolved in lactose) | 0.00 | 0.02 | 3.32 | ND | 0.01 | 96.43 |
| A left in RT for 5 hrs before freeze | 0.01 | 0.03 | 5.67 | 0.02 | 0.02 | 94.03 |
| B left in RT for 5 hrs before freeze | 0.01 | 0.02 | 3.82 | ND | 0.02 | 95.86 |

EXAMPLE 6

6a. Tigecycline (1700 mg) was dissolved in 85 ml of Milli-Q water to form a bulk solution. The pH of the bulk solution was adjusted to about 5.0 with 1.0N HCl. Four aliquots of the bulk solution, each containing about 100 mg tigecycline, were loaded separately into four 20 ml vials containing about 50, 100, 200, and 300 mg of lactose monohydrate respectively. Once the lactose completely dissolved, the samples were lyophilized (frozen at −50° C. by freeze dryers from AdVantage/Virtis) to dryness. The lyophilized samples were placed in a 40° C. 75% RH chamber for 4 days and analyzed by HPLC. The results are summarized in Table 6a and give examples of compositions of the invention.

6b. Tigecycline (400 mg) was dissolved in 20 ml of Milli-Q water to form a bulk solution. The pH of the bulk solution was adjusted to about 5.0 with 1.0N HCl. Three aliquots of the bulk solution, each containing about 100 mg tigecycline, were loaded separately into three 20 ml vials containing 15, 31, and 62 mg lactose monohydrate respectively. Upon dissolution, the samples were lyophilized (frozen at −50° C. by freeze dryers from AdVantage/Virtis) to dryness. The lyophilized samples were placed in a 40° C./75% RH chamber for 20 days and analyzed by HPLC. The results are summarized in Table 6b and show compositions of the invention.

TABLE 6a

| Sample ID (molar ratio) | RRT | | | | | Tigecycline |
|---|---|---|---|---|---|---|
| | 0.5 | 0.55 | Epimer 0.74 | 1.25 MW | 1.67 | |
| | 601 | 583 | 585 | 528 | 556 | 585 |
| pH 5.0 + lactose 50 mg (1:0.81) | ND | 0.04 | 1.01 | ND | ND | 98.53 |
| pH 5.0 + lactose 100 mg (1:1.62) | ND | 0.04 | 0.82 | ND | ND | 98.73 |
| pH 5.0 + lactose 200 mg (1:3.25) | ND | 0.04 | 0.82 | ND | ND | 98.69 |
| pH 5.0 + lactose 300 mg (1:4.87) | ND | 0.04 | 0.87 | ND | ND | 98.64 |

TABLE 6b

| Sample ID (molar ratio) | RRT | | | | | Tigecycline |
|---|---|---|---|---|---|---|
| | 0.5 | 0.55 | Epimer 0.74 | 1.25 MW | 1.67 | |
| | 601 | 583 | 585 | 528 | 556 | 585 |
| pH 5.0 no lactose | 0.03 | 0.07 | 5.40 | 0.02 | 0.07 | 94.19 |
| pH 5.0 + lactose 15 mg(1:0.24) | 0.02 | 0.04 | 3.83 | 0.01 | 0.05 | 95.87 |
| pH 5.0 + lactose 31 mg(1:0.50) | 0.01 | 0.03 | 3.02 | ND | 0.03 | 96.72 |
| pH 5.0 + lactose 62 mg (1:1.00) | 0.01 | 0.03 | 2.18 | ND | 0.02 | 97.61 |

What is claimed is:

1. A composition comprising tigecycline, lactose, and an acid, wherein the molar ratio of tigecycline to lactose is between about 1:1.6 to about 1:3.3, and the pH of the composition in a solution is between about 4.0 and about 5.0, wherein the acid is hydrochloric acid, and the composition further comprises tigecycline epimer in an amount that is not more than 2.56% as measured after storage of the composition at about 40° C. and 75% relative humidity for not more 39 days.

2. The composition of claim 1, wherein the composition is lyophilized.

3. The composition according to claim 1 further comprising a pharmaceutically acceptable diluent.

4. The composition according to claim 3, wherein the pharmaceutically acceptable diluent is water, a saline, Lactated Ringer's Injection solution, or dextrose solution.

5. The composition of claim 1, wherein the pH of the composition in a solution is between 4.2 and about 4.8.

6. A process for preparing a tigecycline composition comprising combining lactose with tigecycline and water to form a solution; reducing the pH of the solution with hydrochloric acid to between about 4.0 and about 5.0; and lyophilizing the solution to dryness to prepare a lyophilized composition;

wherein the lactose is capable of reducing epimer formation of tigecycline whereby the lyophilized composition further comprises tigecycline epimer in an amount that is not more than 2.56% as measured after storage of the lyophilized composition at about 40° C. and 75% relative humidity for not more 39 days, and the molar ratio of tigecycline to lactose is between about 1:1.6 to about 1:3.3.

7. The process of claim 6 further comprising combining the composition with a saline, Lactated Ringer's Injection solution or dextrose solution.

8. The process of claim 6, wherein a solid is formed.

9. The process of claim 6, wherein the pH of the solution is reduced to between about 4.2 and about 4.8.

* * * * *